United States Patent [19]

Sasser

[11] Patent Number: 5,094,720
[45] Date of Patent: Mar. 10, 1992

[54] PROCESS FOR THE DISTILLATIVE PURIFICATION OF CITRAL

[75] Inventor: David E. Sasser, Jacksonville, Fla.

[73] Assignee: Union Camp Corporation, Wayne, N.J.

[21] Appl. No.: 599,762

[22] Filed: Oct. 18, 1990

[51] Int. Cl.$^5$ .................. B01D 3/10; C07C 45/82; C07C 47/21

[52] U.S. Cl. .................................. 203/6; 203/33; 203/34; 203/35; 203/38; 203/91; 568/449; 568/492

[58] Field of Search ............ 203/6, 34, 35, 38, 91, 203/33, DIG. 11; 568/492, 449, 450

[56] References Cited

U.S. PATENT DOCUMENTS

| | | | |
|---|---|---|---|
| 4,288,636 | 9/1981 | Nissen et al. | 568/486 |
| 4,463,196 | 7/1984 | Chabardes et al. | 568/450 |
| 4,467,120 | 8/1984 | Fischer et al. | 568/486 |
| 4,720,327 | 1/1988 | Aquila et al. | 568/913 |
| 4,933,500 | 6/1990 | Chabardes et al. | 568/449 |
| 4,978,804 | 12/1990 | Woell | 568/449 |

FOREIGN PATENT DOCUMENTS 547420  8/1942  United Kingdom ........... 568/492
1381587 1/1975 United Kingdom .

OTHER PUBLICATIONS

Kingston, B. H., "A Fresh Look at Citral", Manufacturing Chemist, Dec. 1962, p. 510.

Primary Examiner—Wilbur Bascomb, Jr.
Attorney, Agent, or Firm—William K. Wissing

[57] ABSTRACT

A method is disclosed for enhancing the purification of citral by fractional distillation by inhibiting the formation of isocitrals from isomerization of citral during the distillation process. The method involves reducing the pH of a mixture containing citral to inhibit the formation of isocitrals from citral upon heating, such as in distillation. Lowering the pH below 7 reduces formation of isocitrals, but a pH of about 4 to 5 is especially preferred. Most preferably, this pH adjustment is accomplished by addition of an acid with a pKa between about 4 and 5.

18 Claims, No Drawings

PROCESS FOR THE DISTILLATIVE PURIFICATION OF CITRAL

FIELD OF THE INVENTION

This invention relates to a distillation process for the purification of citral which inhibits the formation of by-products in the distillation process.

BACKGROUND OF THE INVENTION

Citral is a mixture of aldehydes found in essential oils, specifically lemon grass oil and citronella oil, and is commercially useful as a fragrance for making perfumes, as a flavoring agent, or as an intermediate for other fragrances. Aside from its natural derivation, citral can be produced synthetically.

Citral, as known to those skilled in the art and as used herein, refers to a mixture of geranial and neral. Both the neral and geranial (citral), in turn, have isomer forms known as isocitrals. The isocitrals are low boiling impurities normally found in citral, typically resulting from thermal degradation of the citral.

In one process for producing citral, a thermal rearrangement of beta-pinene yields myrcene, which is an intermediate for many fragrance compounds. Hydrochlorination of the myrcene followed by a displacement reaction utilizing a sodium organic salt, wherein the chloride ions are replaced with an ester group, produces the esters of geraniol and nerol. Subsequent saponification of the esters yields the corresponding alcohols, geraniol and nerol. The alcohols are then oxidized to form the corresponding aldehydes of geranial and neral. The product of this oxidation reaction contains unoxidized nerol and geraniol, neral and geranial (citral), and isomers of the neral and geranial (isocitrals).

Citral may also be produced from petrochemical feedstocks; for example, acetylene, isoprene, or isobutylene. In these reactions, as discussed in U.S. Pat. No. 4,288,636 and Great Britain Patent No. 1,381,587, intermediate materials such as dehydrolinalool and prenal are formed from the petrochemical sources. The intermediate compounds are subsequently converted to citral. While the resultant citral product will not contain nerol and geraniol, it will contain isocitrals.

Adsorptive separation techniques may be used to isolate the citral and isocitral from the unoxidized nerol and geraniol, as is disclosed in U.S. Pat. No. 4,605,783 (Hermann A. Zinnen). However, these adsorptive techniques require both adsorption and desorption of the extract components to and from the absorbent. Furthermore, the adsorptive separation techniques do not address the situation where citral is produced from petrochemical feedstocks, and therefore does not contain unoxidized nerol and geraniol.

A more preferred method for isolation of the citral product from the reaction mixture of the citral process is fractional distillation. However, fractional distillation also has limitations affecting the efficient separation of the citral product from the contaminants. Terpene compounds generally are heat-sensitive, and are subject to degradation unless fractionation is carried out under reduced pressure distillation conditions, thus avoiding excessively high temperatures.

Isocitrals are undesirable because they impart a harsh odor and flavor characteristic to citral. Isocitrals have a lower boiling point than citral. Therefore, this isocitral/citral mixture lends itself to purification through distillation. Since the boiling point of isocitrals is close to that of citral, an efficient selective distillation or fractionation process is required for the separation. The separation is complicated in that isocitrals are formed from citral in an equilibrium process which is directly related to temperature. As a result, attempts to purify citral through fractional distillation to remove isocitrals or other undesirable components results in the formation of additional isocitrals. The amount of isocitrals formed will be directly related to the temperature and the degree of fractionation employed. Thus, the more one attempts to purify citral by fractionation (through the use of more efficient distillation equipment or the use of higher reflux ratios) the more isocitrals will be formed.

Distillation under reduced pressure is helpful in reducing distillation temperatures; however, isocitrals are still formed and high levels of purification (over about 95% citral) are difficult to achieve. Further, such high levels of purity, if achieved by fractional distillation, usually involve a high level of citral conversion to isocitrals, and therefore, the yield of citral is greatly reduced.

Specifically, where citral is being isolated from a mixture or being purified, there are three factors which may affect the purity and yield of citral derived from distillation.

In addition to the heat sensitivity mentioned above, a second factor related to the heat sensitivity of the citral is the equilibrium reaction wherein isocitrals are formed from the citrals. Whether attempting to isolate citral from a reaction solution of a petrochemical or an oxidation citral producing process, when distilling the citral from the reaction solution, the purity and yield of the citral desired will be adversely affected by the isomerization of the citral, resulting in the formation of the isocitrals. Similarly, when attempting to increase the purity of a crude citral solution, the problem of isocitral formation in the distillation process is also present.

A third factor which is encountered in the distillation of citral is citral sensitivity to pH. Citral, being an alpha-beta unsaturated terpene aldehyde, is known to be sensitive to both acidic and basic conditions, as well as temperatures above ambient. Under these conditions citral undergoes a number of reactions which result in not only its loss to residue, but also formation of undesirable components. If the pH of the citral is too low, low citral yields due to high loss of citral to residue during the distillation process can be experienced. Residue as used herein refers to compounds formed from the citral by mechanisms such as dimerization, polymerization, or condensation, for example. These higher molecular weight compounds have higher boiling points than the citral, and as such remain in the kettle during the distillation of the citral from the mixture, thereby decreasing the citral yield. As reported in "A Fresh Look at Citral," by D. H. Kingston, (*Manufacturing Chemist*, Dec. 1962, page 512) citral is very reactive chemically and decomposes readily in the presence of acids or alkali. Kingston reports that paracymene is formed from the citral in the presence of strong acids, and that even under mild acidic conditions structures such as terpineol and terpinolene, and alpha- or beta-cyclocitrals may be formed.

For these reasons, most producers of citral require that the citral remain at a pH of 7 or above. In fact, most of the work performed prior to the surprising discovery of this invention involved the use of a calcium carbonate buffer to ensure that the citral remained at a pH of 7 or slightly higher.

Thus, while fractional distillation may be preferred over adsorptive techniques to separate or purify citral, there is a need to develop a method for fractional distillation which minimizes the production of isocitrals from the citral mixture during the distillation process. At the same time, the method must not reduce the yield of citral through degradation or formation of other compounds.

SUMMARY OF THE INVENTION

The present invention enhances the separation and purification of citral by fractional distillation of the citral from diverse mixtures of citral and other compounds, by inhibiting the isomerization of citral to isocitrals during the distillation process. Surprisingly, and contrary to prior knowledge in the field of citral synthesis, it has been discovered that reducing the pH of a mixture containing citral will inhibit the formation of isocitrals from citral without adversely affecting the yield of citral through degradation or formation of other compounds. Generally, lowering the pH below 7 will reduce formation of isocitrals, but a pH of 4 to 5 is especially preferred. Due to the difficulty of accurately measuring the pH of an oleophilic system, the pH adjustment should be made by addition of an acid with a pKa in the range of 4 to 5. A pH below 3 is not recommended for batch distillation of citral since such a low pH has the result of lowering the yield of citral in such a distillation process. However, lower pH's may be useful if a continuous distillation process is used.

DETAILED DESCRIPTION OF THE INVENTION

An improved method for separation of citral from diverse mixtures and purification of crude citral has been discovered. The mixtures may or may not include isocitrals, and are generally products of processes for producing citral.

In a preferred method, crude citral is produced via the oxidation of nerol and geraniol. Once the oxidation process is complete, the citral is initially purified by removal of residual nerol and geraniol, as well as isocitrals which form during oxidation. Nerol and geraniol, especially nerol, have boiling points very close to citral, making it very difficult to separate geraniol and nerol from citral by distillation.

In order to aid in the separation of the citral, it is desirable to convert the residual nerol and geraniol into other compounds, such as esters of the geraniol and nerol. Those skilled in the art will realize that the esterification of the alcohols may be accomplished by various methods, forming various esters of the geraniol and nerol. These esters are high boiling compounds and are easily separated from citral by distillation. This distillation can also include some fractionation to reduce the isocitral content of the product. This results in a crude citral of approximately 86% to 94% purity. The impurities in this citral include isocitrals, as well as a small percentage both of light ends and high boiling compounds.

The major concern at this point in the process is the isocitrals, which impart an undesirable odor and flavor to the citral. While this crude citral is acceptable for some uses and can be sold and used as is, it is desirable to produce a citral of higher purity with a lower concentration of isocitrals.

Purification of the crude citral is usually accomplished by distillation, since isocitrals are lower boiling than citral. As previously stated, the boiling points of the isocitrals and citral are close together, and therefore a highly efficient fractional distillation process is required for their separation. Upon heating, citral isomerizes to form isocitrals. Generally, distillation of citral takes place under reduced pressure conditions to reduce the distillation temperature and to aid in reducing formation of isocitrals during distillation. This reduces formation of isocitrals; however, further reduction is highly desirable.

Surprisingly, it has been found that reducing the pH of the mixture to between about 3.0 and less than 7.0 before distillation will accomplish the further reduction in the formation of isocitrals during distillation without adversely affecting the yield of citral, which would be expected under acidic conditions. It was discovered that if the citral is neutralized prior to distillation, lower yields of lower purity citral are produced which contain in excess of three times the amount of isocitrals as is found in the feed mixture. When the pH of the citral is adjusted with an acid to about 4.5, higher yields of higher purity citral are produced which contain less isocitral than is contained in the feed mixture.

Citral is known to be sensitive to changes in pH, and in fact if the pH of the citral is too low, low citral yield due to high loss of citral to residue during the distillation process can be experienced. This loss is time dependent, and in shorter operations (such as a continuous operation where the residence time of citral is lower) a lower pH may be used since a shorter residence time leads to lower losses. However, a higher pH, while in the acid range, will minimize this loss to residue. Therefore, it is preferable to maintain a pH in the range of 4 to 5 to optimize lower formation of isocitrals and loss of citral to residue.

Acids which may be used to adjust the pH to between about 3 and less than 7 may be inorganic or organic. One such inorganic acid which may be used to suppress the isomerization of citral to isocitrals during distillation is boric acid. However, it is believed that under certain conditions, orthoboric acid may be converted to metaboric acid, which is more acidic, and would therefore result in large citral losses to residue. Another acid used to suppress the isomerization of citral to isocitrals is phosphoric acid. However, in a manufacturing context, maintaining a pH of 4.5 with a strong acid, such as phosphoric acid with a pKa of 2.12, may be difficult. Alternatively, sodium dihydrogen phosphate may be used to reduce the pH of the citral.

Preferably, since citral is oleophilic, an organic oleophilic acid such as oleic acid can be used to eliminate potential mixing problems between the acid and the citral. Further, an acid with a pKa in the range of about 4 to 5 is best suited for the application. With such an acid, the pH can be adjusted without fear of making the citral too acidic. The acid which is used should have a high boiling point in order to remain in the kettle during distillation. Examples of such acids are ascorbic acid, adipic acid, nicotinic acid, and levulinic acid.

Most preferably, ascorbic acid is used to adjust the pH of citral to between about 4 and 5. Ascorbic acid has two distinct advantages over other acids used, in that it is both a naturally occurring acid and is an acid which has been approved for use in foods. Being a natural acid is very important because high purity citral recovered from essential oils can be classified as a natural product under U.S. regulations when distilled from a natural acid. This is essential if the citral is to be used in pharmaceutical or approved for use in food or flavor ingredients.

While the acids mentioned herein are examples of acids which have been successfully used in the fractional distillation of the citral, they are given as examples and it is not intended to limit the scope of the invention. Acids which are soluble in citral and are of the proper acidity (pKa) which could be added at the distillation step and have a higher boiling point than the citral to ensure that the acid would remain in the kettle throughout the distillation may be used to suppress the isomerization of citral to isocitral in the fractional distillation process.

Citral is oleophilic, and as such its pH is difficult to measure, since most methods for measuring pH are designed to work in aqueous systems. Throughout the tests described herein, the pH of the system was measured by adding a small amount of water (about 5 to 10% by weight) to a sample of the substance to be tested. After mixing and allowing equilibration between the water and the substance, the pH of the water was tested and it was assumed that the pH of the substance was the same. Because of this inherent difficulty of measuring pH in an oleophilic system, it is preferable to adjust the pH using an acid with a pKa in the range of the desired pH. That is, an acid with a pKa below 7 is useful, while a pKa in the range of 4 to 5 is especially preferred for use in this invention.

EXAMPLES

The examples which follow are examples of distillation of impure citral to obtain a high purity (greater than 96%) citral. In each instance, several fractions were taken over the course of the distillation. Since isocitrals are lower boiling than citral, the first fraction was generally high in isocitrals, while the later fractions were higher in citral. The distillation was begun at a reflux ratio of about 10:1 until the isocitral content of the kettle fell below a predetermined level, generally 0.5 to 1.1 % isocitrals. A slightly higher isocitral content (0.7 to 1.1 %) is preferred since fractionation sufficient to produce 0.5% isocitrals would cause an unacceptably high loss of citral to isocitral formation as isocitrals are removed. Once the isocitrals reached the predetermined level, the reflux ratio was reduced to about 1:1 and a product fraction was collected. The fraction was again changed when the levels of undesired high boiling components increased to a predetermined level, generally greater than 0.5% in the overhead, or if the overhead material increased significantly in color. A final fraction was then recovered at recycle ratios of 1:1 to 3:1 until loss of boil-up occurred or the kettle temperature exceeded 175° C.

In many of the examples, the product which would be obtained by combining the most desirable fractions has been calculated. This is to show the quality of the product obtained by the process in a commercial environment, where several fractions would be combined to obtain a greater amount of a citral while maintaining an acceptable purity. Each table also shows the percentage of feed which was residue when the distillation was completed; the amount of material lost to sampling, traps, bleeding, etc.; and the total amount of material accounted for.

For each example, a table has been included showing the results of the distillation. Each table shows the operating conditions during each fraction collected. The conditions recorded are: percent of original feed collected as each fraction; kettle temperature in degrees Celsius during each fraction; overhead temperature in degrees Celsius during each fraction; and the reflux ratio.

Each table then lists the composition of each fraction. The amount of each component as a weight percentage of the fraction is listed. The total citral is listed to show the purity of each fraction. The citral recovery (yield) is shown as the citral in the fraction/by the total citral in the feed, times 100%. Finally, the isocitral balance is shown which is the amount of isocitrals in the fraction divided by the total isocitrals in the feed, times 100%. The total of all isocitrals from all fractions (or in a single fraction) in a given example may total more than 100% of the isocitrals in the feed, since isocitrals may be produced during the distillation. Each table also shows the pH of the starting material and anything which was added to adjust the pH. Where the pH of the feed was calculated, this is also shown.

EXAMPLE 1

Distillation of Citral at a pH of 7.1 versus 4.5

The pH of the feed was 7.1. Only a 94.8% pure citral product was obtained, with a yield of only 60.6%. Further, the total isocitrals produced was extremely high: 3.4 times the isocitrals introduced in the feed. The results are shown in Table 1.

The distillation was repeated, with the addition of Phosphoric acid added to lower the pH to 4.5. A 98.2% pure citral product was obtained, with a yield of 84.1%. A large increase in both citral purity and yield was obtained at the lower pH of 4.5. The results are shown in Table 2.

EXAMPLE 2

Distillation of Citral with 0.2 wt. % Sodium Dihydrogen Phosphate Added

Sodium dihydrogen phosphate was used to reduce the pH of the citral distilled in Example 1 to between about 4 and 5. A 97.7% pure citral was produced at a yield of 84.7%, as shown in Table 3.

EXAMPLE 3

Distillation of Citral in the Presence of Boric Acid

A 97.3% pure citral was produced at a yield of 81.7%, as shown in Table 4.

EXAMPLE 4

Distillation of Citral with 0.2 wt. % Ascorbic Acid (pKa of 4.2 to 4.3) Added

A 98.1% pure citral was produced at a yield of 86.5%, as shown in Table 5.

EXAMPLE 5

Distillation of Citral with 0.2 wt. % Ascorbic Acid Added

A 97.5% pure citral was produced at a yield of 82.8%, as shown in Table 6.

EXAMPLE 6

Distillation of Citral with 0.2 wt. % Levulinic Acid (pKa of 4.6) Added

With some acids that are steam volatile, it is desirable to add the acid after the column has by dried. A 96.4% pure citral was produced at a yield of 82.6%, as shown in Table 7.

EXAMPLE 7

Distillation of Citral with 0.2 wt. % Adipic Acid (pKa of 4.4) Added

A 96.9% pure citral was produced at a yield of 83.0%, as shown in Table 8.

EXAMPLE 8

Distillation of Citral with 0.2 wt. % Century 1030 (Oleic Acid) Added

The use of Century 1030 (Oleic acid) with an estimated pKa of about 4.8 to 5.2 was slightly less effective.

A 96.1% pure citral was produced at a yield of 76.1%, as shown in Table 9.

The next acid tried was salicylic, which has a pKa of 3.0. This acid appeared to suppress isocitral formation; however, the distillation was terminated due to excessive residue formation.

It should be understood that various other modifications will be apparent to and can be readily made by those skilled in the art without departing from the spirit and scope of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof be those skilled in the art to which this invention pertains.

TABLE 1

|  | Feed | Isocitrals Fraction 1 | Isocitrals Fraction 2 | Product Fraction 3 | Fraction 4 | Residue | Total |
|---|---|---|---|---|---|---|---|
| % Charged | 100.0 | 20.5 | 14.5 | 60.0 | 0.7 | 5.5 | 101.2 |
| Kettle Temp (°C.) | N/A | 95 | 99 | 122 | 175 | — | — |
| Ovhd Temp (°C.) | N/A | 51 | 56 | 72 | 69 | — | — |
| Reflux Ratio | N/A | 10:1 | 10–5:1 | 1:1 | 3:1 | — | — |
| ISOCITRALS | 3.0 | 25.1 | 20.3 | 3.8 | 4.4 | — | — |
| Lights | 1.3 | 1.1 | 0.2 | 0.1 | 0.9 | — | — |
| Neral | 37.9 | 60.4 | 59.0 | 18.0 | 2.7 | — | — |
| Geranial | 55.9 | 8.7 | 18.4 | 76.8 | 89.6 | — | — |
| High Boilers | 0.1 | 0.0 | 0.0 | 0.4 | 1.1 | — | — |
| Others | 1.8 | 4.7 | 2.1 | 0.9 | 1.3 | — | — |
| TOTAL CITRAL | 93.8 | 69.1 | 77.4 | 94.8 | 92.3 | — | — |
| Citral Recovery | N/A | 15.1 | 12.0 | 60.6 | 0.7 | — | 88.4 |
| % Isocitral Balance | N/A | 171.5 | 98.1 | 76.0 | 1.0 | — | 346.7 |

Conditions: Citral at pH of 7.1

TABLE 2

|  | Feed | Isocitrals Fraction 1 | Product Fraction 2 | Fraction 3 | Residue | Other (samples, etc) | Total |
|---|---|---|---|---|---|---|---|
| % Charged | 100.0 | 12.9 | 80.1 | 0.5 | 2.2 | 2.9 | 98.7 |
| Kettle Temp (°C.) | N/A | 96 | 117 | 174 | — | — | — |
| Ovhd Temp (°C.) | N/A | 63 | 66 | 84 | — | — | — |
| Reflux Ratio | N/A | 10:1 | 1:1 | 3:1 | — | — | — |
| ISOCITRALS | 2.9 | 17.6 | 0.7 | 1.9 | — | — | — |
| Lights | 0.1 | 2.4 | 0.1 | 0.8 | — | — | — |
| Neral | 37.8 | 68.4 | 32.9 | 4.5 | — | — | — |
| Geranial | 55.7 | 6.3 | 65.3 | 89.0 | — | — | — |
| High Boilers | 0.3 | 0.0 | 0.4 | 1.1 | — | — | — |
| Others | 3.2 | 5.3 | 0.6 | 2.7 | — | — | — |
| TOTAL CITRAL | 93.5 | 74.7 | 98.2 | 93.5 | — | — | — |
| Citral Recovery | N/A | 10.3 | 84.1 | 0.5 | — | — | 94.9 |
| % Isocitral Balance | N/A | 78.3 | 19.3 | 0.3 | — | — | 98.0 |

Conditions: Citral at pH of 7.1 was adjusted to a pH of 4.5 with Phosphoric acid

TABLE 3

|  | Feed | Isocitrals Fraction 1 | Product Fraction 2 | Residue | Others (samples, etc) | Total |
|---|---|---|---|---|---|---|
| % Charged | 100.0 | 11.6 | 81.1 | 2.0 | 4.1 | 98.7 |
| Kettle Temp (°C.) | N/A | 97 | 148 | — | — | — |
| Ovhd Temp (°C.) | N/A | 58 | 67 | — | — | — |
| Reflux Ratio | N/A | 10:1 | 1:1 | — | — | — |
| ISOCITRALS | 2.9 | 17.6 | 0.7 | — | — | — |
| Lights | 0.1 | 3.9 | 0.2 | — | — | — |
| Neral | 37.8 | 66.5 | 34.8 | — | — | — |
| Geranial | 55.7 | 6.8 | 62.9 | — | — | — |
| High Boilers | 0.3 | 0.0 | 0.0 | — | — | — |
| Others | 3.2 | 5.2 | 1.4 | — | — | — |
| TOTAL CITRAL | 93.5 | 73.3 | 97.7 | — | — | — |
| Citral Recovery | N/A | 9.1 | 84.7 | — | — | 93.8 |
| % Isocitral Balance | N/A | 70.4 | 19.6 | — | — | 90.0 |

Conditions: Citral at pH of 7.1 with 0.2 wt % sodium dihydrogen phosphate added

TABLE 4

|  | Feed | Isocitrals Fraction 1 | Product Fraction 2 | Residue | Total |
|---|---|---|---|---|---|
| % Charged | 100.0 | 14.5 | 78.8 | 1.8 | 98.7 |
| Kettle Temp (°C.) | N/A | 95 | 160 | — | — |
| Ovhd Temp (°C.) | N/A | 65 | 67 | — | — |
| Reflux Ratio | N/A | 10:1 | 1-3:1 | — | — |
| ISO-CITRALS | 3.0 | 13.0 | 0.8 | — | — |
| Lights | 1.3 | 2.7 | 0.2 | — | — |
| Neral | 37.9 | 64.6 | 33.6 | — | — |
| Geranial | 55.9 | 14.2 | 63.7 | — | — |
| High Boilers | 0.2 | 0.0 | 0.0 | — | — |
| Others | 1.7 | 5.5 | 1.7 | — | — |
| TOTAL CITRAL | 93.8 | 78.8 | 97.3 | — | — |
| Citral Recovery | N/A | 12.2 | 81.7 | — | 93.9 |
| % Isocitral Balance | N/A | 62.8 | 21.0 | — | 83.8 |

Conditions: Citral at pH of 7.1 with sufficient boric acid present to lower pH to 4.5

TABLE 5

|  | Feed | Isocitrals Fraction 1 | Product Fraction 2 | Residue | Others (samples, etc) | Total |
|---|---|---|---|---|---|---|
| % Charged | 100.0 | 8.7 | 83.7 | 2.2 | 4.2 | 98.8 |
| Kettle Temp (°C.) | N/A | 101 | 180 | — | — | — |
| Ovhd Temp (°C.) | N/A | 67 | 76 | — | — | — |
| Reflux Ratio | N/A | 10:1 | 1:1 | — | — | — |
| ISOCITRALS | 1.9 | 13.3 | 1.0 | — | — | — |
| Lights | 1.1 | 2.1 | 0.1 | — | — | — |
| Neral | 31.6 | 68.9 | 29.9 | — | — | — |
| Geranial | 63.3 | 13.2 | 68.2 | — | — | — |
| High Boilers | 0.9 | 0.0 | 0.4 | — | — | — |
| Others | 1.2 | 2.5 | 0.4 | — | — | — |
| TOTAL CITRAL | 94.9 | 82.1 | 98.1 | — | — | — |
| Citral Recovery | N/A | 7.5 | 86.5 | — | — | 94.0 |
| % Isocitral Balance | N/A | 60.9 | 44.1 | — | — | 105.0 |

Conditions: Citral at pH of 7.1 with 0.2 wt % Ascorbic acid added

TABLE 6

|  | Feed | Isocitrals Fraction 1 | Product Fraction 2 | Residue | Others (samples, etc) | Total |
|---|---|---|---|---|---|---|
| % Charged | 100.0 | 14.8 | 79.3 | 3.3 | 3.3 | 100.8 |
| Kettle Temp (°C.) | N/A | 111 | 158 | — | — | — |
| Ovhd Temp (°C.) | N/A | 87 | 76 | — | — | — |
| Reflux Ratio | N/A | 10:1 | 1:1 | — | — | — |
| ISOCITRALS | 2.8 | 16.1 | 1.1 | — | — | — |
| Lights | 0.9 | 2.8 | 0.1 | — | — | — |
| Neral | 34.9 | 62.0 | 32.1 | — | — | — |
| Geranial | 58.5 | 13.6 | 65.4 | — | — | — |
| High Boilers | 0.9 | 0.0 | 0.2 | — | — | — |
| Others | 2.0 | 5.5 | 1.1 | — | — | — |
| TOTAL CITRAL | 93.4 | 75.6 | 97.5 | — | — | — |
| Citral Recovery | N/A | 12.0 | 82.8 | — | — | 94.8 |
| % Isocitral Balance | N/A | 85.1 | 31.2 | — | — | 116.3 |

Conditions: Citral at pH of 7.1 with 0.2 wt % Ascorbic acid added

TABLE 7

|  | Feed | Isocitrals Fraction 1 | Product Fraction 2 | Fraction 3 | Residue | Other (samples, etc) | Total |
|---|---|---|---|---|---|---|---|
| % Charged | 100.0 | 13.1 | 80.5 | 0.4 | 2.5 | 1.4 | 98.0 |
| Kettle Temp (°C.) | N/A | 105 | 154 | 162 | — | — | — |
| Ovhd Temp (°C.) | N/A | 74 | 78 | 78 | — | — | — |
| Reflux Ratio | N/A | 10:1 | 1:1 | 1:1 | — | — | — |
| ISOCITRALS | 2.9 | 15.0 | 1.7 | 5.8 | — | — | — |
| Lights | 0.7 | 2.2 | 0.1 | 1.3 | — | — | — |
| Neral | 33.8 | 63.2 | 33.6 | 10.4 | — | — | — |
| Geranial | 60.1 | 13.9 | 62.8 | 79.4 | — | — | — |
| High Boilers | 0.4 | 0.0 | 0.2 | 0.8 | — | — | — |
| Others | 2.1 | 5.7 | 1.6 | 2.3 | — | — | — |
| TOTAL CITRAL | 93.9 | 77.1 | 96.4 | 89.8 | — | — | — |
| Citral Recovery | N/A | 10.8 | 82.6 | 0.4 | — | — | 93.8 |
| % Isocitral Balance | N/A | 67.8 | 47.2 | 0.8 | — | — | 115.7 |

Conditions: Citral at pH of 7.1 with 0.2 wt % Levulinic acid added

TABLE 8

|  | Feed | Isocitrals Fraction 1 | Product Fraction 2 | Fraction 3 | Residue | Other (samples, etc) | Total |
|---|---|---|---|---|---|---|---|
| % Charged | 100.0 | 12.6 | 80.4 | 1.0 | 2.4 | 3.0 | 99.4 |

TABLE 8-continued

|  | Feed | Isocitrals Fraction 1 | Product Fraction 2 | Fraction 3 | Residue | Other (samples, etc) | Total |
|---|---|---|---|---|---|---|---|
| Kettle Temp (°C.) | N/A | 106 | 122 | 180 | — | — | — |
| Ovhd Temp (°C.) | N/A | 72 | 78 | 83 | — | — | — |
| Reflux Ratio | N/A | 10:1 | 1:1 | 3:1 | — | — | — |
| ISOCITRALS | 2.9 | 18.3 | 1.3 | 3.9 | — | — | — |
| Lights | 0.7 | 2.5 | 0.1 | 0.7 | — | — | — |
| Neral | 33.8 | 61.2 | 34.1 | 13.2 | — | — | — |
| Geranial | 60.1 | 13.2 | 62.8 | 80.2 | — | — | — |
| High Boilers | 0.4 | 0.0 | 0.2 | 0.1 | — | — | — |
| Others | 2.1 | 4.8 | 1.5 | 1.9 | — | — | — |
| TOTAL CITRAL | 93.9 | 74.4 | 96.9 | 93.4 | — | — | — |
| Citral Recovery | N/A | 10.0 | 83.0 | 1.0 | — | — | 93.9 |
| % Isocitral Balance | N/A | 79.5 | 36.0 | 1.3 | — | — | 116.9 |

Conditions: Citral at pH of 7.1 with 0.2 wt % Adipic acid added

TABLE 9

|  | Feed | Isocitrals Fraction 1 | Product Fraction 2 | Residue | Others (samples, etc) | Total |
|---|---|---|---|---|---|---|
| % Charged | 100.0 | 21.8 | 67.6 | 2.3 | 7.5 | 99.2 |
| Kettle Temp (°C.) | N/A | 93 | 148 | — | — | — |
| Ovhd Temp (°C.) | N/A | 62 | 70 | — | — | — |
| Reflux Ratio | N/A | 10:1 | 1–3:1 | — | — | — |
| ISOCITRALS | 4.0 | 22.6 | 2.6 | — | — | — |
| Lights | 8.0 | 19.8 | 0.1 | — | — | — |
| Neral | 33.8 | 48.8 | 28.6 | — | — | — |
| Geranial | 51.6 | 5.1 | 67.5 | — | — | — |
| High Boilers | 0.6 | 0.1 | 0.8 | — | — | — |
| Others | 1.7 | 3.7 | 1.2 | — | — | — |
| TOTAL CITRAL | 85.4 | 53.9 | 96.1 | — | — | — |
| Citral Recovery | N/A | 13.8 | 76.1 | — | — | 89.9 |
| % Isocitral Balance | N/A | 123.2 | 43.9 | — | — | 167.1 |

Conditions: Citral at pH of 7.1 with 0.2 wt % Century 1030 (Oleic acid) added

What is claimed is:

1. A method for the separation of citral from a mixture containing citral, said method comprising the steps of:
    adjusting the pH of the mixture to between about 3 and less than 7;
    fractionally distilling the resulting mixture to provide a substantially pure citral containing fraction; and recovering the citral containing fraction, wherein the adjusting of the pH substantially inhibits the isomerization of the citral to isocitral during fractional distillation.

2. The method of claim 1 wherein the pH is adjusted to between about 4 and 5.

3. The method of claim 1 wherein the pH is adjusted by adding an organic acid with a pKa between about 4 and 5.

4. The method of claim 3 wherein the acid is selected from the group consisting of ascorbic acid, adipic acid, oleic acid, nicotinic acid, and levulinic acid.

5. The method of claim 4 wherein the acid is ascorbic acid.

6. The method of claim 1 wherein the pH is adjusted by adding an inorganic acid with a pKa between about 4 and 5.

7. The method of claim 6 wherein the acid is selected from the group consisting of boric acid and sodium dihydrogen phosphate.

8. The method of claim 1 wherein the fractional distillation is performed under conditions of reduced pressure.

9. A method for separating citral from a mixture containing isocitrals and citral, said method comprising the steps of:
    adjusting the pH of the mixture to between about 3 and less than 7;
    fractionally distilling the resulting mixture to provide a substantially pure citral containing fraction; and recovering the citral containing fraction, wherein the adjusting of the pH substantially inhibits the isomerization of the citral to isocitral during fractional distillation.

10. The method of claim 9 wherein the pH is adjusted to between about 4 and 5.

11. The method of claim 9 wherein the pH is adjusted by adding an organic acid with a pKa between about 4 and 5.

12. The method of claim 11 wherein the acid is selected from the group consisting of ascorbic acid, adipic acid, oleic acid, nicotinic acid, and levulinic acid.

13. The method of claim 12 wherein the acid is ascorbic acid.

14. The method of claim 9 wherein the pH is adjusted by adding an inorganic acid with a pKa between about 4 and 5.

15. The method of claim 14 wherein the acid is selected from the group consisting of boric acid and sodium dihydrogen phosphate.

16. The method of claim 9 wherein the fractional distillation is performed under conditions of reduced pressure.

17. A method for separating citral from a mixture, said method comprising the steps of:
    adjusting the pH of the mixture to between about 4 and 5 with ascorbic acid;
    fractionally distilling the resulting mixture under conditions of reduced pressure to provide a substantially pure citral containing fraction; and recovering the citral containing fraction, wherein the adjusting of the pH substantially inhibits the isomerization of the citral to isocitral during fractional distillation.

18. In a process for separating citral from a mixture by distillation, the improvement comprising adjusting the pH of the mixture to between about 3 and less then 7, wherein thermally induced formation of isocitrals from the citral is suppressed.

* * * * *